(12) United States Patent
Koehler et al.

(10) Patent No.: US 9,430,832 B2
(45) Date of Patent: Aug. 30, 2016

(54) DIFFERENTIAL PHASE CONTRAST IMAGING WITH ENERGY SENSITIVE DETECTION

(75) Inventors: Thomas Koehler, Norderstedt (DE); Jens-Peter Schlomka, Hamburg (DE)

(73) Assignee: KONINKLIJKE PHILIPS N.V., Eindhoven (NL)

(\*) Notice: Subject to any disclaimer, the term of this patent is extended or adjusted under 35 U.S.C. 154(b) by 189 days.

(21) Appl. No.: 14/240,783

(22) PCT Filed: Aug. 8, 2012

(86) PCT No.: PCT/IB2012/054032
§ 371 (c)(1),
(2), (4) Date: Feb. 25, 2014

(87) PCT Pub. No.: WO2013/030698
PCT Pub. Date: Mar. 7, 2013

(65) Prior Publication Data
US 2014/0205057 A1    Jul. 24, 2014

Related U.S. Application Data

(60) Provisional application No. 61/529,450, filed on Aug. 31, 2011.

(51) Int. Cl.
| | |
|---|---|
| G06K 9/00 | (2006.01) |
| G01N 23/00 | (2006.01) |
| H01J 37/20 | (2006.01) |
| G06T 7/00 | (2006.01) |
| G06T 5/50 | (2006.01) |
| G06T 11/00 | (2006.01) |
| G01N 23/04 | (2006.01) |

(52) U.S. Cl.
CPC ........... *G06T 7/0014* (2013.01); *G01N 23/046* (2013.01); *G06T 5/50* (2013.01); *G06T 11/005* (2013.01); *G06T 2211/408* (2013.01)

(58) Field of Classification Search
None
See application file for complete search history.

(56) References Cited

U.S. PATENT DOCUMENTS

| | | | | |
|---|---|---|---|---|
| 6,526,121 | B1 * | 2/2003 | Hwu | A61B 6/4092 378/62 |
| 8,306,183 | B2 * | 11/2012 | Koehler | A61B 6/00 378/36 |
| 2004/0062452 | A1 | 4/2004 | Sakaida | |

(Continued)

FOREIGN PATENT DOCUMENTS

| | | |
|---|---|---|
| EP | 1731099 | 12/2006 |
| WO | WO2010146503 | 12/2010 |

OTHER PUBLICATIONS

G. Fornaro et al., "Global and local Phase-UnWrapping Techniques: A Comparison", J. Opt. Soc. Am. A/vol. 14, No. 10, Oct. 1997, pp. 2702-2708.

(Continued)

*Primary Examiner* — Randolph I Chu

(57) ABSTRACT

For correcting differential phase image data 52, differential phase image data 52 acquired with radiation at different energy levels is received, wherein the differential phase image data 52 comprises pixels 60, each pixel 60 having a phase gradient value 62a, 62b, 62c for each energy level. After that an energy dependent behavior of phase gradient values 62a, 62b, 62c of a pixel 60 is determined and a corrected phase gradient value 68 for the pixel 60 is determined from the phase gradient values 62a, 62b, 62c of the pixel 60 and a model for the energy dependence of the phase gradient values 62a, 62b, 62c.

14 Claims, 3 Drawing Sheets

(56) References Cited

U.S. PATENT DOCUMENTS

| | | | | |
|---|---|---|---|---|
| 2007/0189449 | A1* | 8/2007 | Baumann | A61B 6/484 378/44 |
| 2007/0223799 | A1* | 9/2007 | Weiss | B60R 25/00 382/131 |
| 2008/0299588 | A1* | 12/2008 | Gorski | G01N 33/6887 435/7.21 |
| 2009/0128830 | A1* | 5/2009 | Kottler | G01B 15/025 356/521 |
| 2010/0272230 | A1* | 10/2010 | Koehler | A61B 6/00 378/36 |
| 2011/0025691 | A1* | 2/2011 | Hempel | A61B 6/484 345/424 |
| 2011/0206187 | A1* | 8/2011 | Lee | B82Y 10/00 378/122 |
| 2012/0183197 | A1* | 7/2012 | Gleich | A61B 6/4241 382/132 |
| 2013/0028378 | A1* | 1/2013 | Stutman | G01N 23/04 378/62 |
| 2013/0064469 | A1* | 3/2013 | Koehler | G06T 5/50 382/261 |
| 2013/0345138 | A1* | 12/2013 | Pentyala | C07K 7/08 514/16.9 |
| 2014/0146945 | A1* | 5/2014 | Fredenberg | A61B 6/4233 378/62 |

OTHER PUBLICATIONS

W. Haas et al., "Phase-Unwrapping of Differential Phase-Contrast Data Using Attenuation Information", Proc. of SPIE vol. 7962, 2011, pp. 79624R-1-79624R-6.

C. Kottler et al., "Dual Energy Contrast X-Ray Imaging With Talbot-Lau Interferometer", Journal of Applied Physics 108, (2010), pp. 114906-1-114906-6.

C. Kottler et al., "A Two-Directional Approach for Grating Based Differential Phase Contrast Imaging Using Hard X-Rays", Optics Express, vol. 15, No. 3, Feb. 5, 2007, pp. 1175-1181.

* cited by examiner

DIFFERENTIAL PHASE CONTRAST IMAGING WITH ENERGY SENSITIVE DETECTION

CROSS-REFERENCE TO PRIOR APPLICATIONS

This application is the U.S. National Phase application under 35 U.S.C. §371 of International Application Serial No. PCT/IB2012/054032, filed on Aug. 8, 2012, which claims the benefit of U.S. Application Ser. No. 61/529,450, filed on Aug. 31, 2011. These applications are hereby incorporated by reference herein.

FIELD OF THE INVENTION

The invention relates to differential phase contrast imaging. In particular, the invention relates to a method for correcting differential phase image data, a method for generating corrected differential phase image data, a computer program, a computer readable medium and differential phase imaging system.

BACKGROUND OF THE INVENTION

X-ray radiography and tomography are important methods for a variety of applications, for example non-destructive investigation of bulk samples, quality inspection of industrial products and non-invasive examination of anatomical structures and tissue regions of interest in the interior of a patient's body.

X-ray imaging based on attenuation of X-rays may yield excellent results where highly absorbing anatomical structures such as bones are embedded in a tissue of relatively weakly absorbing material. This is due to the fact that the penetration depth of hard X-ray beams may be rather high, which allows for recording sharp projections of the attenuation coefficient.

When different kinds of tissue with similar absorption cross-sections are under examination (for example in mammography or angiography), the contrast of X-ray absorption may be relatively poor. In this case, phase contrast X-ray radiography and tomography may be employed, where the change of phase of the X-rays penetrating the object of interest is examined. One method to obtain phase contrast information is the so-call differential phase contrast imaging as described in the following.

In differential phase contrast X-ray radiography and tomography, phase wrapping may occur. If the gradient of the phase front is outside the range of [−π; π] per grating period, the gradient is wrapped into this interval. This situation may appear in particular at the rim of an object, for example because of a big jump of the refractive index between air and tissue. The phase wrapping may happen for reasonable grating pitches of 2 µm for the phase grid already for object sizes below 1 mm. In particular in differential phase contrast X-ray tomography, this may lead to a strong capping artifact in the reconstructed image.

SUMMARY OF THE INVENTION

It is an object of the invention to provide images recorded with differential phase contrast X-ray imaging, in particular tomography, that illustrate and represent the imaged object of interest clearly and exactly.

This object is achieved by the subject-matter of the independent claims. Further exemplary embodiments are evident from the dependent claims and the following description.

A first aspect of the invention relates to a method for correcting differential phase image data. For example, the method may be applied in X-ray phase contrast imaging, in particular mammography.

According to an embodiment of the invention, the method comprising the steps of: Receiving differential phase image data acquired with radiation at different energy levels, wherein the differential phase image data comprises pixels, each pixel having a phase gradient value for each energy level; Determining an energy dependent behavior of phase gradient values of a pixel; Determining a corrected phase gradient value for the pixel from the phase gradient values of the pixel and a model for the energy dependence of the phase gradient values. With the method, phase unwrapping in differential phase contrast CT by using energy sensitive detection is possible. The method may be performed pixel per pixel, i.e. locally.

For example, with the model for the energy dependence of the phase gradient value, a wrapping number at the pixel may be determined from the energy dependent behavior. The wrapping number, i.e. the number of complete shifting by $2\pi$ of the phase of the radiation at the position of the pixel, may be determined by using the differential phase image data acquired at different energy levels, i.e. at different wave lengths of the radiation. Every pixel of the differential phase image data is associated with phase gradient values, for example at least three values, from which the energy dependent behavior of the phase gradient at the pixel may be determined. Since the energy dependent behavior is characteristic for the wrapping number, the wrapping number at the pixel may be determined. With the wrapping number, a corrected phase gradient value at a selected reference energy may be determined and corrected differential phase image data may be generated from the corrected pixels.

In such a way, artifacts in the image data that are based on phase wrapping during the detection process may be reduced or eliminated from the image data.

A further aspect of the invention is a method for generating corrected differential phase image data.

According to an embodiment of the invention, the method comprises integrating the differential data to obtain either a plain phase contrast image (radiograph) of the object or the facilitate image fusion with the attenuation contrast image.

According to an embodiment of the invention, the method comprises the steps of: Generating radiation at different energy levels; detecting the generated radiation penetrating an object of interest; Acquiring or recording differential phase image data from the detected radiation; and executing the steps of the method for correcting differential phase image data as described in the above and in the following.

A further aspect of the invention relates to a differential phase imaging system, for example a CT system.

According to an embodiment of the invention, the system comprises a radiation source, a detector and a controller, wherein the radiation source is adapted to generate radiation of different energy levels, wherein the detector is adapted to detect differential phase image data of an object of interest penetrated by the radiation, wherein the controller is adapted to carry out the method as described in the above and in the following.

Further aspects of the invention are a computer program for correcting differential phase image data or for generating corrected differential phase image data and a computer-readable medium on which such a computer program is stored.

It has to be understood that features of the method as described in the above and in the following may be features of the system, the computer program and the computer readable medium as described in the above and in the following.

These and other aspects of the invention will be apparent from and elucidated with reference to the embodiments described hereinafter.

BRIEF DESCRIPTION OF THE DRAWINGS

Below, embodiments of the present invention are described in more detail with reference to the attached drawings.

In principle, identical parts are provided with the same reference symbols in the figures.

DETAILED DESCRIPTION OF EMBODIMENTS

Figure 1:
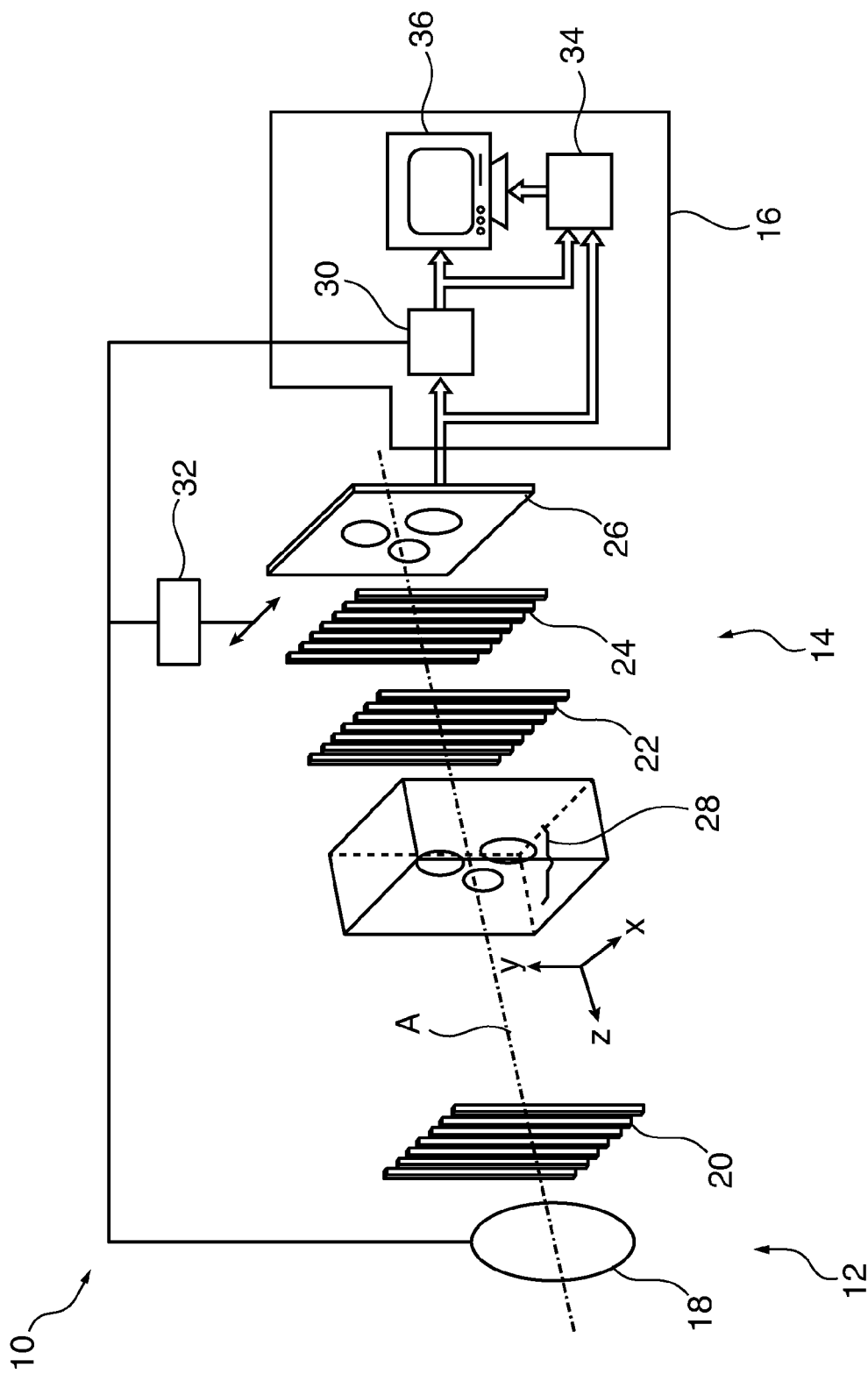
FIG. 1 schematically shows a differential phase imaging system according to an embodiment of the invention.

FIG. 1 schematically shows a differential phase imaging system 10 with a radiation source 10, a detector 12 and a controller 14.

The radiation source 10 may comprise an incoherent X-ray source 16, for example an X-ray tube 18, and a source grating 20 for achieving spatial beam coherence. The radiation source 10 may be adapted to generate a spatial coherent beam of radiation.

The detector 12 may comprise a phase grating 22, an absorber grating 24 and an X-ray detector element 26 adapted for detecting image data from X-rays radiated from the radiation source through an object of interest 28.

The source grating 20, the phase grating 22 and the absorber grating 24 have a plurality of equidistant X-ray absorbing (source and absorber grating) or phase shifting (phase grating) strips which extend in parallel in a direction normal to an optical axis A of the imaging system 10.

The phase grating 22 serves as a phase-shifting beam splitter, which transforms the variation of the phase front of the x-ray beam into an intensity modulation, i.e., an interference pattern with a typical length scale of half the pitch of the phase grating 22 at the location of the absorber grating 24. The absorber grating 24 generates a Moire interference pattern from the X-rays leaving the phase grating 22. The Moire interference pattern on the detector element 26 contains information about the phase shift of the deflected and phase-shifted X-rays after passing both the object 28 and the phase grating 22.

The controller 16 comprises a processor 30 for recording or acquiring the image data from the detector element 26 and for commanding and/or controlling a motor 32 for moving the absorber grating 24 in a direction orthogonal to the extension of the strips of the gratings 22, 24. Due to the movement of the absorber grating 26 different Moire patterns are generated on the detector element 26. These different Moire patterns may be recorded by the processor 30 and transformed into differential phase image data, which may be stored into memory 34 of the controller 14.

The controller 16 and in particular the processor 30 may be further adapted to control the incoherent X-ray source 16 in such a way that different energy levels of X-rays are generated. For example, the tube voltage of an X-ray tube 16 may be adjusted in such a way that different energy levels of X-rays are generated.

Summarized, the differential phase imaging system 10 may comprise a radiation source 12, a detector 14 and a controller 16. The radiation source 10 may be adapted to generate radiation of different energy levels, the detector 14 may be adapted to detect data of an object of interest 28 penetrated by the radiation. The data may be transformed to differential phase image data by the controller 16.

Furthermore, the differential phase imaging system 10 is adapted for acquiring image data at different energy levels of the X-ray radiation. In other words, the acquisition of the image data may be energy sensitive.

On the one hand this may be achieved by controlling the radiation source 12 to generate X-rays at different energy levels at different time points, for example by altering the tube voltage with the controller 16 and with a detector that is sensitive to all generated energy levels. In this case several measurements (at different time points) with different settings for the tube voltage and/or beam filtration may be made for generating the image data.

On the other hand an energy sensitive acquisition may be achieved with an radiation source 12 that generates simultaneously different energy levels of radiation and a detector 14 that is adapted for differentiating between different energy levels, for example a spectroscopic detector.

It may be possible that the system 10 is an X-ray differential phase contrast radiography system 10 and/or an X-ray differential phase contrast tomography system 10. In the later case, the system 10 may calculate slices or three dimensional representations from the object 18 from image data that has been acquired from different directions by moving the arrangement of radiation source 12 and detector 14 and the object 28 relative to each other.

The generated radiography or tomography images may be displayed on a display 36 of the system 10.

Due to the spatial variation of the refractive index $\delta(x,y,z)$ of the object 28, two different beams of x-rays through the object 28 may undergo different phase changes in its phase, which may be detected with the detector 12 and differential phase image data may be calculated from the detected raw data with the processor 30 and stored in the memory 34.

However, with the detector 14 and the following transformation process of the raw data, the phase gradient cannot be determined unambiguously. In other words, when the real phase gradient is outside the interval $[-\pi, \pi]$ the determined phase gradient is wrapped to this interval, i.e. only the real phase gradient modulo $2\pi$ may be determined.

The ambiguity of the determined phase gradient may be resolved by the use of energy sensitive acquisition in combination with a spectral model of the measurement process, which will be explained in the following.

The dependence of the real part of the refractive index $\delta$ can be described using a potential law $$\delta(E) = \left(\frac{E_0}{E}\right)^2 \delta(E_0).$$

Since the phase of the wave-front φ of a beam of radiation along the z-direction is approximately $$\varphi(x, y, E) = -\frac{2\pi E}{hc} \int_{-\infty}^{0} \delta(x, y, z', E) dz',$$

the absolute phase gradient g of the wave front has the following dependence on the energy, i.e. the wavelength $$g(E) = \frac{\partial}{\partial x}\varphi(E) = \frac{E_0}{E}\frac{\partial}{\partial x}\varphi(E_0)$$

This may be viewed as a model of the energy behavior of the phase gradient.

Figure 2:
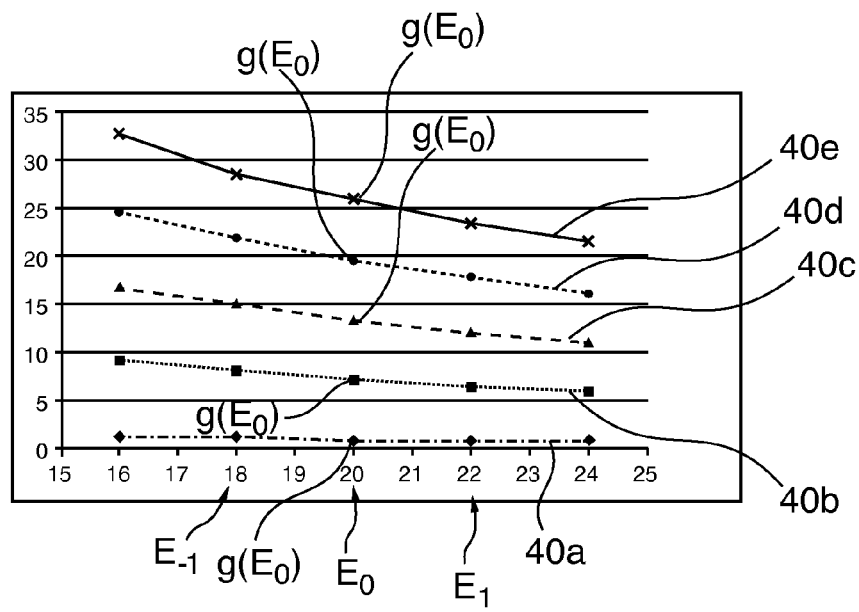
FIG. 2 shows a diagram with absolute phase gradient values according to an embodiment of the invention.

FIG. 2 shows a diagram with true phase gradient values for different energies and shows the energy dependence of the phase gradient. The x-axis of the diagram depicts the energy in keV, the y-axis the absolute phase gradient in rad. FIG. 2 illustrates the dependency of the phase gradient for different values. Five curves 40a, 40b, 40c, 40d and 40e are illustrated which are selected such that the gradient $g(E_0)$ at the design energy $E_0=20$ keV is $g(E_0)=(1+n\pi)/(\text{grid spacing of the phase grid } 22)$ with n=0, 2, 4, 6, 8. The curve 40a belongs to n=0, the curve 40b to n=2 and so on. Due to the choice of the above formula for the curves 40a, 40b, 40c, 40d, 40e, the phase gradient values $g(E_0)$ at $E_0=20$ keV differ by $2\pi$.

However, the detected (measured) and determined differential phase image data does not comprise the absolute (true) phase gradient values, but the values that are wrapped to the interval $[-\pi, \pi]$.

Figure 3:
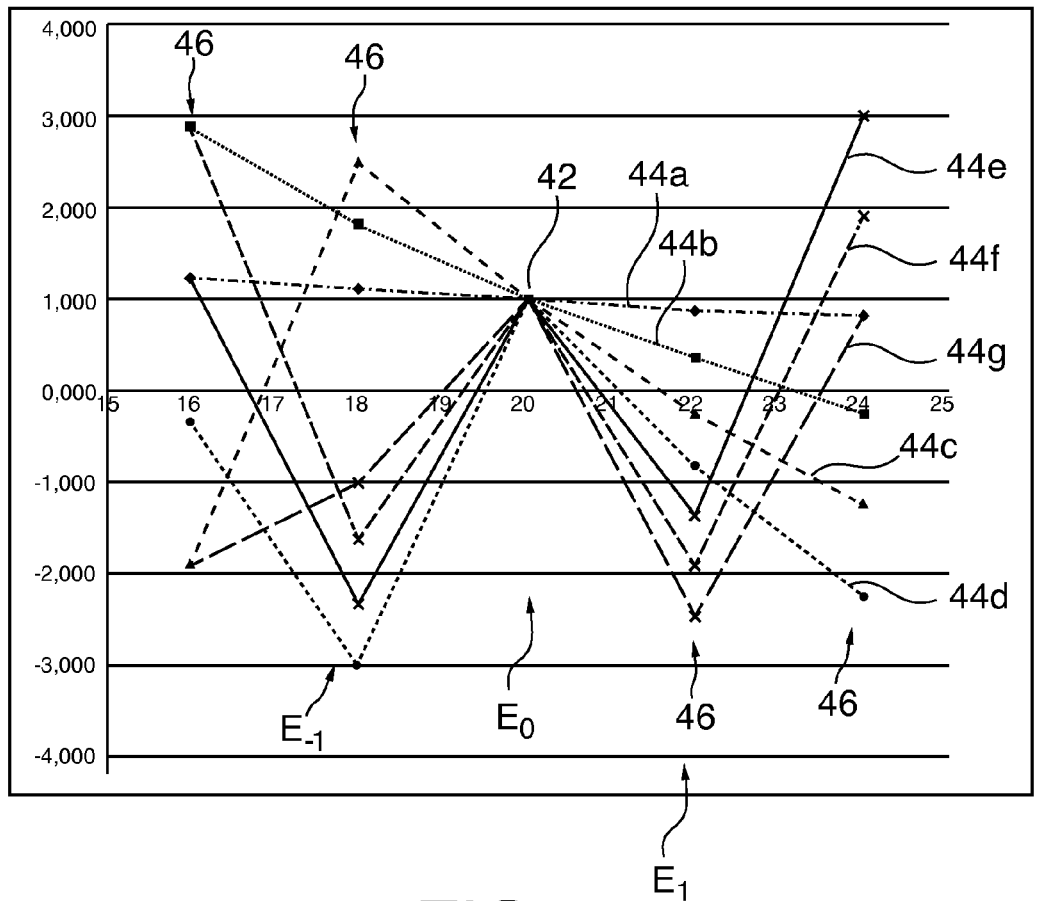
FIG. 3 shows a diagram with wrapped phase gradient values according to an embodiment of the invention.

This is depicted with respect to FIG. 3, which shows a diagram with wrapped phase gradient values. The x-axis of the diagram depicts the energy in keV, the y-axis the wrapped phase gradient in rad. The wrapped phase gradient values related to the same value for n are connected by lines for illustration purpose.

In FIG. 3, the true phase gradients 40a, 40b, 40c, 40d, 40e from FIG. 2 are wrapped into the interval $[-\pi; \pi]$ per grating period into relative phase gradients 44a, 44b, 44c, 44d, 44e, 44f, 44g. The curves 44a, 44b, 44c, 44d, 44e, 44f, 44g belong to the numbers n=0, 2, 4, 6, 8, 10, 12, respectively.

In the diagram, the data points or curve 44a relate to the case where no wrapping occurred. The curve 44a shows the expected $E_0/E$ scaling around the phase gradient of 1 rad/grid period. The data points or curve 44b relate to a true phase gradient of $(1+2\pi)/\text{grid}$ period at 20 keV, which is wrapped to 1 rad/grid period. Since the difference of the phase gradient between 20 keV and, e.g. 22 keV is based on the true gradient, the wrapped phase gradient changes quicker with energy, which makes an unwrapping possible.

Since the phase gradients $g(E_0)$ were selected to differ by $2\pi$, the wrapping causes that at $E_0$, all wrapped (i.e. measured) phase gradients 42 are the same. Even though the wrapped curves 44a, 44b, 44c, 44d, 44e, 44f, 44g (that represent measured values) suffer from phase wrapping at the other energies as well for n>0, it is clearly visible that different numbers n of wrapping result in quite different distributions of wrapped phase gradients 46 within the energy range shown.

In particular, all the curves 44a, 44b, 44c, 44d, 44e, 44f, 44g have different wrapped phase gradients 46 at different energy levels (for example 16 keV, 18 keV, 22 keV, 24 keV) for several gradient curves 44a, 44b, 44c, 44d, 44e, 44f, 44g which are mapped all to the same value 42 at the design or reference energy (for example 20 keV).

Even three data points 42, 46 (and therefore three measurements at three different energy levels) may be sufficient to distinguish all cases (i.e. curves 44a, 44b, 44c, 44d, 44e, 44f, 44g) shown in FIG. 3, for instance the data points of the energy levels $E_{-1}$, $E_0$ and $E_1$ corresponding to 18, 20, and 22 keV.

Figure 4:
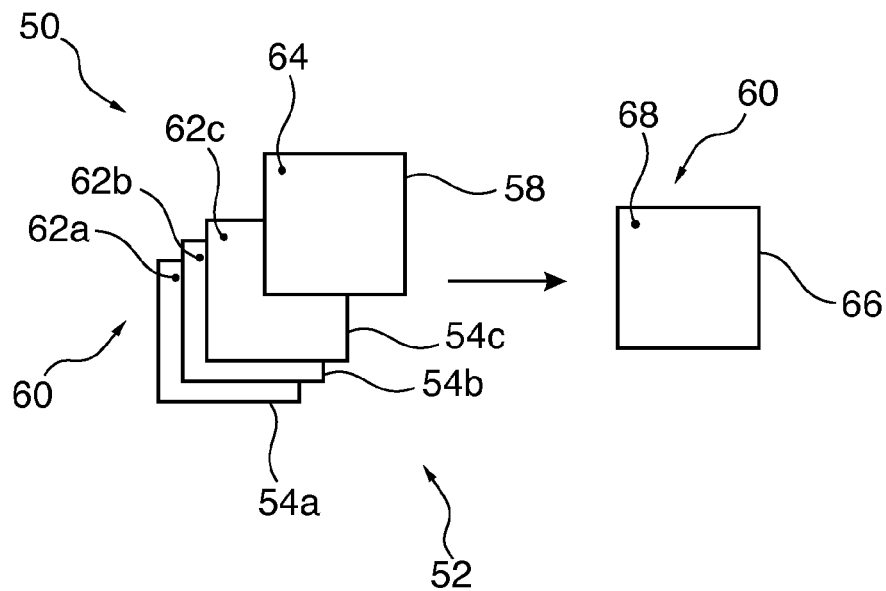
FIG. 4 schematically shows image data according to an embodiment of the invention.

FIG. 4 schematically shows image data 50 that may be received, processed, and stored in the memory 34 of the controller 16 and in particular by the processor 30.

The image data 50 may comprise differential phase image data 52, comprising differential phase image data 54a, 54b, 54c acquired at different energy levels $E_{-1}$, $E_0$, $E_1$, respectively and/or may comprise attenuation image data 58.

The image data 50 is composed of pixels 60 and each pixel may have a phase gradient value 62a, 62b, 62c for each energy level $E_{-1}$, $E_0$ and $E_1$ and/or an attenuation value 64.

According to an embodiment of the invention, a pixel 60 has phase gradient values 62a, 62b, 62c corresponding to at least three energy levels $E_{-1}$, $E_0$ and $E_1$.

According to an embodiment of the invention, a pixel 60 has an attenuation value 64.

The image data 50 may comprise corrected differential phase image data 66, that may be generated from the image data 52, 58 by the method as described in the above and in the following. In particular, every pixel 60 may comprise a corrected phase gradient value 68 that may be determined from the values 62a, 62b, 62c, 64 by the method.

It has to be noted that the image data 50 need not represent two dimensional images. Other representations, for example, line data may be possible. In other words, the detector element 26 may be a two dimensional detector or a line detector.

Figure 5:
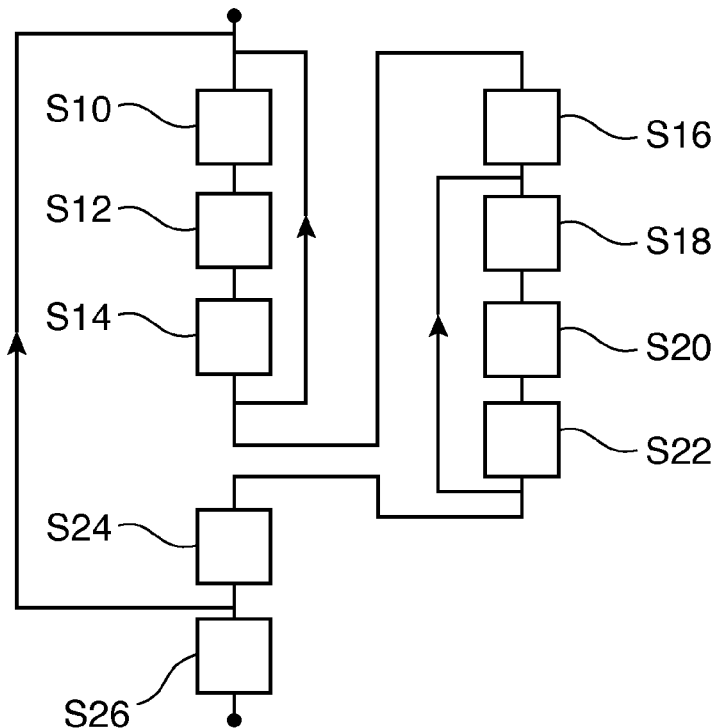
FIG. 5 shows a flow diagram for a method for generating and correction differential phase image data according to an embodiment of the invention.

FIG. 5 shows a flow diagram for a method for generating and correction differential phase image data 52.

In step S10, the radiation source 12 is controlled by the controller 16 to generate a radiation at a first energy level $E_{-1}$, for example X-ray radiation of 18 keV. The radiation penetrates the object 28 and falls onto the detector 26.

According to an embodiment of the invention, the radiation is electromagnetic radiation, for example, x-ray radiation.

In step S12, the controller 16 controls the detector 14, and in particular the grating 24, such that different Moire interference patterns are detected by the detector element 26.

According to an embodiment of the invention, the method comprises the step of detecting the generated radiation penetrating an object of interest 28.

In step S14, the Moire interference patterns are transformed into differential phase image data 52a and attenuation image data 58 by the processor 30. These image data 52a, 58 may be stored in the memory 34.

According to an embodiment of the invention, the method comprises the step of acquiring differential phase image data 52 from the detected radiation.

The steps S10 to S14 are repeated for every further energy level $E_0$, $E_{-1}$. The attenuation image data 58 may be acquired for only one energy level, for example the basic energy level $E_0$.

According to an embodiment of the invention, the method comprises the step of generating radiation at different energy levels $E_{-1}$, $E_0$, $E_1$.

According to an embodiment of the invention, the energy levels $E_{-1}$, $E_0$, $E_1$ of the radiation comprise a reference energy level $E_0$ and two neighboring energy levels $E_{-1}$, $E_1$ differing about 8% to 12%, e.g. 10%, from the reference energy level $E_0$, for example 18, 20 and 22 keV.

It may be possible that the radiation at one energy level is generated at different time points and the radiation is detected at these different time points, as explained above. However, it may also be possible, that radiation with different energy levels is simultaneously generated and detected, for example with a multi-chromatic radiation source 12 and a spectroscopic detector 14.

In step S16, the image data 50 is received by the processor 30 from the memory 34 (for example pixel wise).

According to an embodiment of the invention, the method comprises the step of receiving differential phase image data 52 acquired with radiation at different energy levels $E_{-1}$, $E_0$, $E_1$, wherein the differential phase image data 52 comprises pixels 60, each pixel 60 having a phase gradient value 62a, 62b, 62c for each energy level $E_{-1}$, $E_0$, $E_1$ and optionally an attenuation value 64.

The following steps S18 to S22 may then be repeated for every pixel 60 of the image data 50.

In step S18, the energy dependent behavior of the phase gradient values 62a, 62b, 62c of the selected pixel 60 is determined with the aid of the wrapping curves 44a to 44g shown in FIG. 3.

According to an embodiment of the invention, the method comprises the step of determining an energy dependent behavior 44a to 44g of phase gradient values 62a, 62b, 62c of a pixel 60.

The wrapping curves 44a to 44g may be represented in the memory 30 with data points 41, 46. For example, for every curve 44a to 44g at least three precalculated data values 42, 46 may be stored.

According to an embodiment of the invention, a wrapping curve 44a to 44g is represented by phase gradient values 42, 46 associated with energy levels $E_{-1}$, $E_0$, $E_1$.

According to an embodiment of the invention, the phase gradient values 42, 46 of a wrapping curve 44a to 44g are precalculated and/or stored in the controller 16, for example the memory 34.

According to an embodiment of the invention, the phase gradient values 42, 46 of the wrapping curves 44a to 44g are determined such that phase gradient values 42 at a reference energy level $E_0$ are equal. The phase gradient values 62a, 62b, 62c may then, by the processor 30, be mapped to every wrapping curve stored in the controller 16. For example, for each wrapping curve 44a to 44g, a best fitting value is calculated, that indicates how much the phase gradient values 62a, 62b, 62c of the pixel correspond to the wrapping curve 44a to 44g. In particular, a phase gradient value 62a, 62b, 62c of the pixel 60 may be mapped to the corresponding phase gradient values 42, 46 of a wrapping curve. After that a numerical fit may be calculated from the mapped values 62a, 62b, 62c, 42, 46.

According to an embodiment of the invention, the energy dependent behavior is determined by fitting the phase gradient values 62a, 62b, 62c of the pixel 60 to a plurality of phase wrapping curves 44a to 44g.

According to an embodiment of the invention, a phase gradient value 42, 46 of an energy level $E_{-1}$, $E_0$, $E_1$ of a wrapping curve 44a to 44g is fitted with a phase gradient value 62a, 62b, 62c of the pixel 60 at this energy level.

According to an embodiment of the invention, the fitting is a numerical fitting, for example a fitting with a root mean square measure.

In step S18, the processor 30 may determine a wrapping number n for the pixel 60 with the aid of the best fit of the phase gradient values 62a, 62b, 62c to the wrapping curves 44a to 44g. Since each wrapping curve may be associated with a wrapping number, the wrapping number n for the pixel may be chosen as the wrapping number of the wrapping curve with the best fit.

According to an embodiment of the invention, the method comprises the step of determining a wrapping number n of the pixel 60 from the energy dependent behavior.

According to an embodiment of the invention, the wrapping number n of the pixel 60 is determined by determining a wrapping curve 44a to 44g with a best fit of the fitted phase gradient values 62a, 62b, 62c of the pixel 60 and by selecting the wrapping number associated with the determined wrapping curve 44a to 44g.

Alternatively or additionally, the phase gradient value may be determined directly from the model of the energy behavior of the phase gradient.

According to an embodiment of the invention, the phase gradient value 42 at $E_0$ is denoted as $g_0$ and is calculated by the least squares fit $$g = \mathrm{argmin}_g \sum_i \frac{1}{\sigma_i^2} \left\| w\left(\frac{E_0}{E_i}\tilde{g}\right) - g_i \right\|_\pi^2$$

where $\sigma^2$ are the variances of the measured wrapped phase gradient values $g_i$ at energies $E_i$, w denotes the wrapping operation, and $\|\cdot\|_\pi$ denotes a special distance operation namely $$\|d\|_\pi = \begin{cases} |d + 2\pi| & \text{for } d < -\pi \\ |d| & \text{for } -\pi \leq d \leq \pi \\ |d - 2\pi| & \text{for } d > \pi \end{cases}$$

Summarized, for every meaningful wrapping number n (for example 0, 2, 4, . . . , 12) a numerical fit may be made to get the best fitting $g(E_0)$ assuming that the phase wrapped n/2 times at $E_0$. Finally, among these results the one with the best overall fit (using for instance a root mean square measure) may be picked or chosen.

In step S20, the processor 30 determines the absolute or corrected phase gradient value 68 from the determined wrapping number n. For example to the phase gradient value 62b at the reference energy level $E_0$, nπ may be added for calculating the value 68.

According to an embodiment of the invention, the method comprises the step of determining a corrected phase gradient value 68 for the pixel 60 from the phase gradient values 62a, 62b, 62c of the pixel 60 and the wrapping number of the pixel 60.

According to an embodiment of the invention, the corrected phase gradient value 68 is determined by shifting the phase gradient value 62b of the pixel 60 associated with a reference energy level $E_0$ with the determined wrapping number of the pixel 60.

When not preselecting the plurality of wrapping curves 44a to 44g, the method may only allows distinguishing between reasonably small values for possible wrapping values n. If n become excessively large, however, the results may become ambiguous again. In this situation, the attenuation image 58 may provide a rough estimate of the wrapping number n. The attenuation image 58 may then be used to resolve the remaining uncertainty.

Optionally, in step S18, the gradient value at the pixel 60 of the attenuation image data 58 may be determined with the processor 30. From the gradient value, meaningful wrapping numbers (for example n=20 to 30) may be determined. For example, a function or table is stored in the memory 34, with which a gradient value may be mapped to an estimated region of wrapping numbers.

The plurality of wrapping curves is then delimited to wrapping curves associated with wrapping numbers in that region.

According to an embodiment of the invention, the phase gradient is obtained by a least squares fit $$g = argmin_{\tilde{g}} \left( \sum_i \frac{1}{\sigma_i^2} \left\| w\left(\frac{E_0}{E_i}\tilde{g}\right) - g_i \right\|_\pi^2 + P(\tilde{g}) \right)$$

Where the penalty function P is used to define an admissible range $-g_{max}$ to $g_{max}$ for the result, e.g. by using a discrete penalty $$P(\tilde{g}) = \begin{cases} 0 & \text{for } |\tilde{g}| < g_{max} \\ \infty & \text{else} \end{cases}$$

or $$P(\tilde{g}) = |\tilde{g}/g_{max}|^m$$

for a large value of m to approximate the discrete penalty with a smooth function. In the aforementioned case where the wrapping number is estimated from the attenuation image to be e.g. in the order of $n_0$, which is equivalent for g to be in the order of $n\pi$, the penalty can be selected to be $$P(\tilde{g}) = \begin{cases} 0 & \text{for } |\tilde{g} - n_0\pi| < g_{max} \\ \infty & \text{else} \end{cases}$$

or $$P(\tilde{g}) = |(\tilde{g} - n_0\pi)/g_{max}|^m.$$

According to an embodiment of the invention, the method comprises the step of determining the gradient of the attenuation value 64 at the pixel 60.

According to an embodiment of the invention, the method comprises the step of choosing an estimated region of wrapping numbers.

In step S20 then, optionally only the chosen wrapping curves are used for the fitting of the phase gradient values 62a, 62b, 62c of the pixel 60.

According to an embodiment of the invention, the method comprises the step of fitting the phase gradient values 62a, 62b, 62c of a pixel 60 to a plurality of wrapping curves 44a to 44g associated with wrapping numbers in the estimated region.

If the system 10 is a tomography system 10, the system may generate image data showing slices or three dimensional views of the object 28. The image data may be displayed on display 36 of the controller 16.

In this case, the differential phase image data 52 may be acquired in different directions with respect to the object 18.

Thus, in step S24 the controller 16 may change the optical axis A with respect to the object, for example by rotating the arrangement of radiation source 12 and detector 14 around the object 18 and may repeat the acquisition of image data 50 with respect to the changed direction.

After enough image data 50 has been acquired and corrected, the controller 16 and in particular the processor 30 may generate tomography image data in step S26.

According to an embodiment of the invention, the method comprises the step of generating tomography image data from the corrected differential phase image data 66.

It has to be understood that the steps of FIG. 5 need not be performed in the order as described with respect to FIG. 5.

Note further that a distinction between different values 62a, 62b, 62c, 42, 46 may require that the signal-to-noise ratio must be roughly large enough to distinguish correctly between different data points. More specifically, for measurement at the design energy $E_0$, and a further measurement at $E_0+\Delta E$, the phase gradients differ by $$g(E) - g(E_0) = \frac{E_0}{E_0 + \Delta E} g(E_0) - g(E_0) \approx \frac{\Delta E}{E_0} g(E_0).$$

Since the gradients to be distinguished by the proposed method may differ by $2\pi$/per grating period, the signal-to-noise ratio may have to allow for a distinction of (wrapped) phase gradient differences of $$\Delta g \approx -\frac{\Delta E}{E_0} 2\pi$$

Depending on the object 28, the energy spacing between the energy levels $E_{-1}$, $E_0$, $E_1$ used in the method can be tuned to achieve this.

The method as described in the above and the following may be a computer program executed in the processor 30 and stored in the memory 34. The computer program may be stored in a computer-readable medium like a floppy disk, a hard disk, an USB (Universal Serial Bus) storage device, a RAM (Random Access Memory), a ROM (Read Only memory) and an EPROM (Erasable Programmable Read Only Memory). A computer readable medium may also be a data communication network, e.g. the Internet, which allows downloading a program code.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practising the claimed invention, from a study of the drawings, the disclosure, and the appended claims. In the claims, the word "comprising" does not exclude other elements or steps, and the indefinite article "a" or "an" does not exclude a plurality. A single processor or controller or other unit may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:
1. A method for correcting differential phase image data (52), the method comprising the steps of
Receiving differential phase image data (52) acquired with radiation at different energy levels ($E_{-1}$, $E_0$, $E_1$), wherein the differential phase image data (52) com- prises pixels (60), each pixel (60) having a phase gradient value (62a, 62b, 62c) for each energy level ($E_{-1}$, $E_0$, $E_1$);

Determining an energy dependent behavior (44a to 44g) of phase gradient values (62a, 62b, 62c) of a pixel (60);

Determining a corrected phase gradient value (68) for the pixel (60) from the phase gradient values (62a, 62b, 62c) of the pixel (60) and a model for the energy dependence of the phase gradient values (62a, 62b, 62c).

2. The method of claim 1,
wherein the energy dependent behavior is determined by fitting the phase gradient values (62a, 62b, 62c) of the pixel (60) to a plurality of phase wrapping curves (44a to 44g), each wrapping curve being associated with a wrapping number;
wherein the wrapping number of the pixel (60) is determined by determining a wrapping curve (44a to 44g) with a best fit of the fitted phase gradient values (62a, 62b, 62c) of the pixel (60) and by selecting the wrapping number associated with the determined wrapping curve (44a to 44g).

3. The method of claim 2,
wherein a wrapping curve (44a to 44g) is represented by phase gradient values (42, 46) associated with energy levels ($E_{-1}$, $E_0$, $E_1$);
wherein a phase gradient value (42, 46) of an energy level ($E_{-1}$, $E_0$, $E_1$) of a wrapping curve (44a to 44g) is fitted with a phase gradient value (62a, 62b, 62c) of the pixel (60) at this energy level.

4. The method of claim 3,
wherein the phase gradient values (42, 46) of the wrapping curves (44a to 44g) are determined such that phase gradient values (42) at a reference energy level ($E_0$) are equal.

5. The method of claim 1,
wherein the pixel (60) has an attenuation value (64);
wherein the method comprises the steps of:
Determining the gradient of the attenuation value (64) at the pixel (60);
Choosing an estimated region of wrapping numbers;
Fitting the phase gradient values (62a, 62b, 62c) of a pixel (60) to a plurality of wrapping curves (44a to 44g) associated with wrapping numbers in the estimated region.

6. The method claim 1,
wherein the corrected phase gradient value (68) is determined by shifting the phase gradient value (62b) of the pixel (60) associated with a reference energy level ($E_0$) with the determined wrapping number of the pixel (60).

7. The method of claim 1,
wherein a pixel has phase gradient values (62a, 62b, 62c) corresponding to at least three energy levels ($E_{-1}$, $E_0$, $E_1$).

8. The method of claim 1,
wherein the radiation is electromagnetic radiation.

9. The method of claim 1,
wherein the energy levels $E_{-1}$, $E_0$, $E_1$ of the radiation comprise a reference energy level ($E_0$) and two neighboring energy levels ($E_{-1}$, $E_1$) differing from 8% to 12% from the reference energy level ($E_0$).

10. A method for generating corrected differential phase image data (66), the method comprising the steps:
Generating radiation at different energy levels ($E_{-1}$, $E_0$, $E_1$);
Detecting the generated radiation penetrating an object of interest (28);
Acquiring differential phase image data (52) from the detected radiation;
Executing the steps of claim 1 with the generated differential phase image data (52).

11. The method of claim 10,
wherein the differential phase image data is acquired in different directions with respect to the object of interest;
wherein the method comprises the step of:
Generating tomography image data from the corrected differential phase image data.

12. A non-transitory computer-readable storage medium having stored therein machine readable instructions configured to be executed by a processor for correcting differential phase image data (52), which, when executed by the processor (30), is adapted to carry out the steps of claim 1.

13. A differential phase imaging system (10), comprising:
a radiation source (12);
a detector (14); and
a controller (16);
wherein the radiation source (12) is adapted to generate radiation of different energy levels;
wherein the detector (14) is adapted to detect differential phase image data (52) of an object of interest (28) penetrated by the radiation;
wherein the controller (16) is adapted to carry out the method according to claim 1.

14. The differential phase imaging system (10) of claim 13,
wherein the differential phase imaging system is an X-ray CT system (10).

* * * * *